(12) United States Patent
Omidbakhsh

(10) Patent No.: US 8,591,958 B2
(45) Date of Patent: Nov. 26, 2013

(54) CONCENTRATED HYDROGEN PEROXIDE DISINFECTING SOLUTIONS

(75) Inventor: Navid Omidbakhsh, Cherry Hill, NJ (US)

(73) Assignee: Virox Technologies Inc., Ontario (CA)

( * ) Notice: Subject to any disclaimer, the term of this patent is extended or adjusted under 35 U.S.C. 154(b) by 0 days.

(21) Appl. No.: 13/120,746

(22) PCT Filed: Sep. 30, 2009

(86) PCT No.: PCT/CA2009/001376
§ 371 (c)(1),
(2), (4) Date: Jul. 1, 2011

(87) PCT Pub. No.: WO2010/037219
PCT Pub. Date: Apr. 8, 2010

(65) Prior Publication Data
US 2011/0262557 A1    Oct. 27, 2011

Related U.S. Application Data

(60) Provisional application No. 61/136,746, filed on Sep. 30, 2008.

(51) Int. Cl.
*A01N 39/00*    (2006.01)
*A01N 25/00*    (2006.01)
*A61K 33/40*    (2006.01)

(52) U.S. Cl.
USPC ............................ 424/616; 424/613; 424/405

(58) Field of Classification Search
USPC ....................................................... 424/616
See application file for complete search history.

(56) References Cited

U.S. PATENT DOCUMENTS

| | | | | | |
|---|---|---|---|---|---|
| 3,925,241 | A | * | 12/1975 | Schmolka | ...................... 516/104 |
| 4,356,100 | A | * | 10/1982 | Sherman | ...................... 510/112 |
| 6,530,384 | B1 | | 3/2003 | Meyers et al. | |
| 7,354,604 | B2 | * | 4/2008 | Ramirez et al. | ............... 424/616 |
| 7,632,523 | B2 | * | 12/2009 | Ramirez et al. | ............... 424/616 |
| 2002/0168422 | A1 | | 11/2002 | Hei et al. | |
| 2005/0058719 | A1 | * | 3/2005 | Ramirez et al. | ............... 424/616 |
| 2007/0059380 | A1 | | 3/2007 | Ramirez et al. | |

FOREIGN PATENT DOCUMENTS

| CA | 2503627 | 6/2004 |
|---|---|---|
| CA | 2584421 | 5/2006 |

* cited by examiner

*Primary Examiner* — Cherie M Stanfield
*Assistant Examiner* — Mark V Stevens
(74) *Attorney, Agent, or Firm* — Clark & Brody

(57) ABSTRACT

A concentrated and one phase cleaning and disinfecting solution containing a sparingly soluble cyclic carboxylic acid. The solution has a pH of from about 0.05 to about 2, and comprises, consists essentially of, or consists of from about 2% w/w to about 8% w/w hydrogen peroxide; from about 5% w/w to about 20% w/w linear alkyl benzene sulfonic acid; from about 0.5% w/w to about 8% w/w of at least one sparingly soluble (i.e. a solubility in pure water at room temperature of less than 1% w/w) cyclic carboxylic acid, wherein the cyclic carboxylic acid is present in acid and salt form in a ratio of at least 9:1 (acid:salt); from about 2% w/w to about 10% w/w of at least one block copolymer surfactant (e.g. PLURONIC L62); and from about 4% w/w to about 15% w/w of at least one solvent.

12 Claims, No Drawings

CONCENTRATED HYDROGEN PEROXIDE DISINFECTING SOLUTIONS

FIELD

This invention relates to disinfectants and, in particular, it relates to a hydrogen peroxide-based disinfectant concentrate suitable for use in preparing hydrogen peroxide disinfecting solutions.

BACKGROUND

In the past few years, a tremendous effort has been made to develop disinfectants that are environmentally-friendly, effective against microorganisms when diluted, and non-toxic to humans and animals. Hydrogen peroxide is environmentally-friendly as its decomposition products, namely oxygen and water, are generally benign. It has been used for many years in various applications due to, at least in part, its broad spectrum of antimicrobial activity. This characteristic is particularly important in situations where harmful organisms are present but their identity is not known.

One of the primary drawbacks of hydrogen peroxide is that its antimicrobial action is too slow at low concentrations. For example, known references indicate that a 0.1% w/w aqueous solution of hydrogen peroxide requires about 60 minutes to disinfect surfaces contaminated with *Staphylococcus aureus*, whereas, under the same test conditions, a 25.8% w/w aqueous solution of hydrogen peroxide requires only about 20 seconds. The latter solution may not be practical or economically viable. It may be subject to hazardous goods regulations and require special precautions for handling and use. A second major drawback is that stabilizers typically used to stabilize hydrogen peroxide in solution, namely, phosphorus-based stabilizers, may deposit and accumulate in rivers and lakes and contribute to their eutrophication.

Solutions containing less than about 8% w/w hydrogen peroxide are preferred for their improved safety profile. For example, at concentrations of above about 8% w/w aqueous solution, hydrogen peroxide is considered corrosive and a strong oxidizing agent. At concentrations of about 3-7% w/w aqueous solution, hydrogen peroxide is considered non-corrosive but an eye irritant. At concentrations of about 1-3% w/w aqueous solution, hydrogen peroxide is considered non-corrosive and non-irritating.

Attempts have been made to enhance the disinfecting activity of hydrogen peroxide solutions. For example, peracid combined with hydrogen peroxide can increase the disinfectant activity of hydrogen peroxide significantly. However the disadvantage of such compositions is their corrosiveness, poor safety profile, and pungent smell. Increased activity can be also achieved by combining hydrogen peroxide with heavy metals to release hydroxyl radicals. Unfortunately, such solutions demonstrate poor stability, and should be prepared in situ.

Sparingly water soluble cyclic carboxylic acids have been shown to enhance the disinfecting activity of solutions containing hydrogen peroxide and certain anionic surfactants (e.g. dodecyl benzene sulfonic acid). It is possible to make ready-to-use products with a combination of these ingredients, with the cyclic carboxylic acid present in low concentrations. However, making concentrated versions of these solutions is a challenge, due to the low solubility of the cyclic carboxylic acids in aqueous solutions. At higher concentrations, such acids precipitate out of solution. This makes it difficult to prepare diluted, ready-to-use solutions that are of a uniform character and provide consistent performance from the concentrated solution. As concentrated solutions are easier and less costly to ship, it is desirable to make solutions comprising sparingly soluble cyclic carboxylic acids, hydrogen peroxide and anionic surfactants in concentrated form.

One way to do this is to add high quantities of solvent or emulsifiers to solubilize the acid in solution. However, this can be undesirable for the following reasons. Many solvents are considered volatile organic compounds (VOCs) which are not favorable from an environmental point of view. Furthermore, they can serve to reduce the flash point of the solution and increase its hazard rating. Using high levels of emulsifiers can leave a residue that produces streaking and tackiness on surfaces or devices after drying.

Another approach to making concentrated solutions containing a sparing soluble cyclic carboxylic acid, hydrogen peroxide, and an anionic surfactant is to increase the pH to increase the solubility of the acid in solution, partially turning it into its salt form which is more water soluble. However, since such acids tend to act better in their acid form, increasing the pH can reduce the antimicrobial effectiveness of the solution.

There is therefore a need for a stable, concentrated, hydrogen peroxide-based cleaning and disinfecting solution containing one or more anionic surfactants and one or more sparingly soluble cyclic carboxylic acids, which solution can be diluted prior to use. Preferably, the solution is not flammable, does not leave high amounts of residue after being applied to a surface after dilution, and is efficacious and fast-acting at high dilutions.

SUMMARY

The inventor has found that sparingly soluble cyclic carboxylic acids can be dissolved in acidic (i.e. pH≤2), aqueous solutions containing hydrogen peroxide, a linear alkyl benzene sulfonic acid, and a block copolymer surfactant. This enables the preparation of concentrated hydrogen peroxide based and carboxylic acid based solutions that do not require high solvent concentrations and which are efficacious after dilution.

According to a first aspect of the invention, there is provided a concentrated and stable cleaning and disinfecting solution having a pH of from about 0.05 to about 2, comprising, consisting essentially of, or consisting of:
  a. from about 2% w/w to about 8% w/w hydrogen peroxide;
  b. from about 5% w/w to about 20% w/w of at least one linear alkyl benzene sulfonic acid (e.g. C8-C16 linear alkyl aryl sulfonic acid);
  c. from about 0.5% w/w to about 8% w/w of at least one sparingly soluble cyclic carboxylic acid, wherein the cyclic carboxylic acid is present in acid and salt form in a ratio of at least 9:1 (acid:salt);
  d. from about 2% w/w to about 10% w/w of at least one block copolymer surfactant; and
  e. from about 4% w/w to about 15% w/w of at least one solvent;
     wherein the solution is stable.

The pH of the solution may range from about 0.05 to about 1, from about 0.2 to about 2, and from about 0.2 to about 1.

The hydrogen peroxide may be present in a concentration of from about 4% w/w to about 7.5% w/w, and from about 3% w/w to about 8% w/w.

The linear alkyl benzene sulfonic acid may be present in a concentration of from about 7% w/w to about 15% w/w C8-C16 and may be dodecylbenzene sulfonic acid.

The at least one sparingly soluble cyclic carboxylic acid may be present in a concentration of from about 2% w/w to about 3.5% w/w and may be chosen from benzoic acid and benzoic acid derivatives (e.g. salicylic acid).

The at least one block copolymer surfactant may be may be present in a concentration of from about 3% w/w to about 7% w/w and may be chosen from (A)-(B)-(A) or (B)-(A)-(B) or

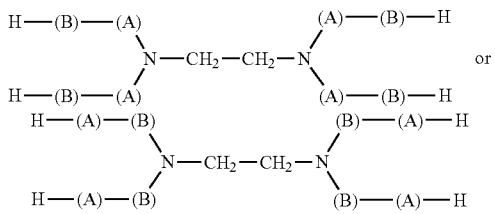

wherein A represents a block of propylene oxide repeating units and B represents a block of ethylene oxide repeating units, and wherein the block copolymer surfactant has a molecular weight of from 1500 to 30000 Daltons. (e.g. PLURONIC L62).

The solvent may be present in a concentration of from about 4% w/w to about 15% w/w and may be chosen from glycol ethers, short chain alcohols having from 1 to 8 carbon atoms, benzyl alcohol, and phenoxy ethanol. The glycol ethers may be chosen from propylene glycol n-propyl ether, dipropylene glycol n-propyl ether, propylene glycol methyl ether, dipropylene glycol methyl ether, tripropylene glycol monomethyl ether, dipropylene glycol n-propyl ether, tripropylene glycol n-propyl ether, dipropylene glycol n-butyl ether, tripropylene glycol n-butyl ether, ethylene glycol monobutyl ether, ethylene glycol monohexyl ether, and diethylene glycol monobutyl ether.

The solution may further comprise, consist essentially of, or consist of one or more of the following ingredients (a) from about 0.1% w/w to about 20% w/w of another anionic surfactant; (b) from about 0.1% w/w to about 20% w/w of a hydrogen peroxide stabilizer or chelating agent; (c) from about 0.1% w/w to about 10% w/w of another non-ionic surfactant; (d) from about 0.01% w/w to about 10% w/w of a buffering agent; (e) from about 0.1% w/w to about 10% w/w of a corrosion inhibitor; (e) from about 0.05% w/w to about 5% w/w of another carboxylic acid; and (f) other additives to make the solutions more marketable (e.g. colouring agents and fragrances). DK In some embodiments, the solution has a pH of from about 0.05 to about 1.5, and comprises, consists essentially of, or consists of:
a. from about 2% w/w to about 8% w/w hydrogen peroxide;
b. from about 8% w/w to about 12% w/w dodecyl benzene sulfonic acid;
c. from about 2% w/w to about 3% w/w salicylic acid;
d. from about 4% w/w to about 6% w/w PLURONIC L62;
e. from about 7% w/w to about 9% w/w propylene glycol n-propyl ether;
f. from 0% w/w to about 0.1% w/w 1-hydroxyethylidene-1,1,-diphosphonic acid;
g. from 0% w/w to about 0.1% w/w C10 alkylated sulfonated diphenyl oxide disodium salt;
h. from 0% w/w to about 3% w/w phosphoric acid; and
i. from about 0.1% w/w to about 1% w/w benzotriazole.

In other embodiments, the solution is phosphorus free, has a pH of from about 0.05 to about 2, and comprises, consists essentially of, or consists of:

a. from about 2% w/w to about 8% w/w hydrogen peroxide;
b. from about 5% w/w to about 20% w/w of at least one C8-C16 alkyl aryl sulfonic acid;
c. from about 0.5% w/w to about 8% w/w of at least one sparingly soluble cyclic carboxylic acid, wherein the cyclic carboxylic acid is present in acid and salt form in a ratio of at least 9:1 (acid:salt);
d. from about 2% w/w to about 10% w/w of at least one block copolymer surfactant; and
e. from about 4% w/w to about 15% w/w of at least one solvent.

In still further embodiments, the solution is phosphorus free, has a pH of less than about 1.5, and comprises, consists essentially of, or consists of:
a. from about 2% w/w to about 8% w/w hydrogen peroxide;
b. from about 8% w/w to about 12% w/w dodecyl benzene sulfonic acid;
c. from about 2% w/w to about 3% w/w salicylic acid;
d. from about 4% w/w to about 6% w/w PLURONIC L62; and
e. from about 7% w/w to about 9% w/w of at least one solvent.

The invention also provides, in accordance with another aspect, a solution according to the first aspect, diluted with water at a ratio of from 1:10 to 1:1000 (solution:water).

DETAILED DESCRIPTION OF EMBODIMENTS

The term "comprising," when used in relation to a number of integers or elements, means including without being limited to the recited integers or elements. The term "consisting essentially of" means including the recited integers or elements (and normal impurities present therein) and such additional integers or elements that do not materially affect the basic and novel properties of the invention. "Basic and novel properties of the invention" refers to the solubility and stability of the invention. Solutions that are one-phase are contemplated as being within the scope of the present invention. Conversely, solutions that are in two or more phases shall be understood to be outside the scope of the present invention.

The term "consisting of" means including only the recited integers or elements and no additional integers or elements, except those that may be present as normal impurities.

The expression of quantity in terms of "% w/w" means the percentage by weight, relative to the weight of the total solution or composition, unless otherwise specified.

The term "about" when used to modify a specified numeric value or quantity refers to variations in the numeric value or quantity that can occur by virtue of (a) typical measuring and liquid handling procedures that are used to make concentrates; (b) differences in the manufacture, source, or purity of the ingredients employed to make the present solutions, and the like. The term "about" also encompasses variations in value or quantity that may occur due to different equilibrium conditions of the present solutions. Whether or not modified by the term "about," the claims include equivalents to the specified values or quantities.

The term "stable solution" shall be construed to mean a solution that retains at least 90% of its initial hydrogen peroxide concentration for at least one year at room temperature, and does not precipitate or separate in phases throughout its shelf life even after a cycle of freeze/thaw.

The singular forms, "a," "an," and "the" include plural forms unless content clearly dictates otherwise. Thus, for example, a composition containing "a compound" may include a mixture of two or more compounds. It should also be noted that the term "or" is generally employed in the sense of "and/or" unless the content clearly dictates otherwise.

The term "low soluble" or "sparingly soluble" means a solubility in pure water at room temperature of less than 1% w/w.

All concentration values given herein are concentration values pertaining to concentrated solutions according to the invention, unless otherwise specified, or unless the context dictates otherwise.

Sparingly Soluble Cyclic Carboxylic Acids

The sparingly soluble cyclic carboxylic acids useful herein may be chosen from benzoic acid and benzoic acid derivatives, including 2-hydroxybenzoic acid (i.e. salicylic acid), 3-hydroxybenzoic acid, 4-hydroxybenzoic acid, and dihydroxy benzoic acid. The water solubility of such compounds can be found in chemistry references such as the Merck Index. For benzoic acid and salicylic acid, the water solubility at 20° C. is 0.29% and 0.2%, respectively.

These carboxylic acids can be used at concentrations from about 0.5% w/w to about 8% w/w. Alternatively, minimum concentrations of about 1.5% w/w, about 2% w/w, and about 2.5% w/w are possible. Similarly, maximum concentrations of about 7% w/w, about 6% w/w, about 5% w/w, about 4% w/w and about 3.5% w/w are also contemplated.

Non-Ionic Surfactants

The block copolymers employed in embodiments of the invention are non-ionic surfactants. Classes of suitable block copolymer surfactants have structures generally represented by $(PO)_y\text{-}(EO)_x\text{—}(PO)_y$, and $(EO)_x\text{—}(PO)_y\text{-}(EO)_x$. Alternatively, they can be shown as: (A)-(B)-(A) and (B)-(A)-(B) where A represents a block of propylene oxide repeating units and B represents a block of ethylene oxide repeating units. The block copolymers useful in the present invention have an average molecular weight of from about 1500 to about 10000. Table 1 (below) shows some exemplary surfactants from BASF Corporation (Florham Park, N.J. sold in association with the trademark PLURONIC). These surfactants can be used at concentrations from about 2% w/w to about 10% w/w. Alternatively, minimum concentrations of about 3% w/w, about 4% w/w, and about 5% w/w are possible. Similarly, maximum concentrations of about 8% w/w, about 7% w/w, about 6% w/w, and about 5.5% w/w are also contemplated.

TABLE 1

Examples of suitable Pluronic block copolymers

| Pluronic | Average Molecular weight (Da) | Total weight of PO units | EO %** |
|---|---|---|---|
| 17R2 | 2150 | 1700 | 20% |
| 17R4 | 2650 | 1700 | 40% |
| 25R2 | 3100 | 2500 | 20% |
| 31R1 | 3250 | 3100 | 10% |
| L43 | 1850 | 1300 | 30% |
| L44 | 2200 | 1320 | 40% |
| L61 | 2000 | 1800 | 10% |
| L62 | 2500 | 2000 | 20% |
| L64 | 2900 | 1740 | 40% |
| F68 | 8400 | 1700 | 80% |
| L81 | 2750 | 2500 | 10% |
| L101 | 3800 | 3400 | 10% |

**EO % = ethylene oxide %

Poloxamines are another useful class of block copolymer surfactant. They are tetrafunctional ethylene oxide/propylene oxide block copolymers bonded to an ethylene diamine central group via the propylene oxide moiety resulting in four blocks per ethylene diamine molecule. Poloxamines are also referred to as ethylene diamine alkoxylates, N,N_,N_,N_-tetra[(oxyethylene)-(oxypropylene)]diaminoethylenes, sold in association with the trademarks Tetronics™ and Synperonic™. The average molecular weight of the poloxamines ranges from 1500 to 30000. Low average molecular weight poloxamines are viscous oils or pastes; the higher molecular weight counterparts are amorphous solids. Poloxamines have numerous uses in industry as the size of both the POE and POP blocks can be easily and independently altered, giving rise to variations in hydrophilic/hydrophobic balance as well as total molecular weight of the copolymers. These surfactants have the following general structures:

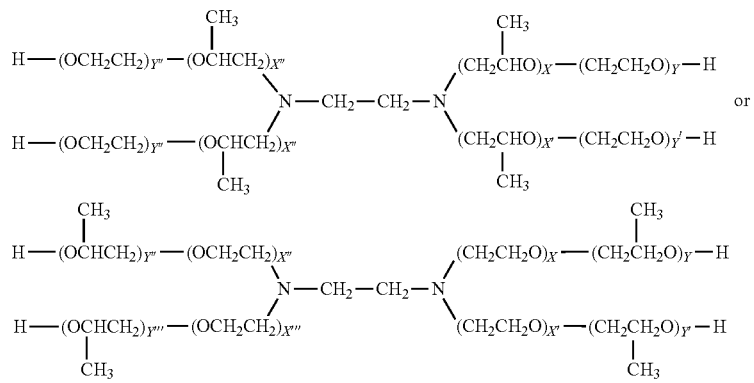

The above can be shown alternatively as:

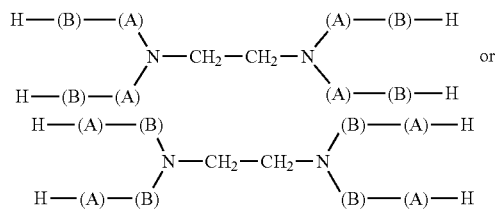

wherein A represents a block of propylene oxide repeating units and B represents a block of ethylene oxide repeating units, and wherein the molecular weight of the block copolymer is from 1500 to 30000.

Examples of suitable poloxamines are Tetronic 1301, 104, 1307, 150R1, 701, 901, 904, 908 from BASF Corporation. Additional examples are provided in Table 2.

TABLE 2

Examples of suitable Tetronic block copolymers

| Tetronic | Average Molecular weight (Da) | Total weight of PO units (Da) | EO % |
|---|---|---|---|
| 304 | 1650 | 990 | 40% |
| 701 | 3600 | 3240 | 10% |
| 704 | 5500 | 3300 | 40% |
| 803 | 5500 | 3850 | 30% |
| 901 | 4700 | 4230 | 10% |
| 904 | 6700 | 4020 | 40% |
| 908 | 25000 | 5000 | 80% |
| 1107 | 15000 | 4500 | 70% |
| 1301 | 6800 | 6120 | 10% |
| 1304 | 10500 | 6300 | 40% |
| 1307 | 18000 | 5400 | 70% |
| 150R | 8000 | 7200 | 10% |

Hydrogen Peroxide

The hydrogen peroxide concentration in the concentrated solution may range from about 2% w/w to about 8% w/w. Alternative minimum concentrations of about 3% w/w, 3.5% w/w, about 4% w/w, about 4.5% w/w, and about 5% w/w, are also contemplated. Alternative maximum concentrations of about 7.5% w/w, about 7% w/w, and about 6.5% w/w are possible.

Anionic Surfactant

Linear alkyl benzene sulfonic acids enhance the cleaning and disinfecting activity of the hydrogen peroxide solution. In combination with the sparingly soluble cyclic carboxylic acids, these anionic surfactants also provide the acidity required to perform effectively at high dilutions, without the need for additional acids. The linear alkyl benzene sulfonic acid may be chosen from C8-C16 alkyl benzene sulfonic acids. The linear alkyl benzene sulfonic acid may be dodecyl benzene sulfonic acid. In combination with a solvent and block-copolymers, they play a role in solubilizing the sparingly soluble cyclic carboxylic acids.

The linear alkyl benzene sulfonic acid is present in the concentrated solution at a concentration of from about 5% w/w to about 20% w/w. Alternatively, minimum concentrations of about 6% w/w, about 7% w/w, about 10% w/w, and about 14% w/w are contemplated. Similarly, maximum concentrations of about 19% w/w, about 17% w/w, about 15% w/w, about 14% w/w, about 12% w/w and about 10% w/w are contemplated.

Solvents

Solvents are used in a concentration of from about 4% w/w to about 15% w/w. Alternatively, minimum concentrations of about 5% w/w, about 6% w/w, and about 7% w/w are contemplated. Similarly, maximum concentrations of about 10% w/w, about 9% w/w, and about 8% w/w are contemplated. Non-limiting examples of solvents are short-chain alcohols, glycol ethers and derivatives thereof, and aromatic alcohols.

Suitable short chain alcohols are generally C1-C8 alcohols including, but not limited to, methanol, ethanol, iso-propanol, n-butanol and n-pentanol.

Propylene glycol n-propyl ether (Dowanol PnP™, Dow Chemical) is an exemplary glycol ether for use as a solvent. Other suitable glycol ethers include but no limited to dipropylene glycol n-propyl ether, propylene glycol methyl ether, dipropylene glycol methyl ether, tripropylene glycol monomethyl ether, dipropylene glycol n-propyl ether, tripropylene glycol n-propyl ether, dipropylene glycol n-butyl ether, tripropylene glycol n-butyl ether, ethylene glycol monobutyl ether, ethylene glycol monohexyl ether, and diethylene glycol monobutyl ether. These products are available from The Dow Chemical Company, (Midland, Mich.) and are sold in association with the trademark Dowanol. Of aromatic alcohols, benzyl alcohol and phenoxy ethanol are exemplary solvents. A further useful solvent is 3-methoxy-3-methyl-1-butanol (MMB). Suitable solvents also include non-flammable solvents, those being solvents with flash points of greater than 37° C. Preferred solvents are those with higher flash points.

The following ingredients can be optionally used in solutions according to the invention.

Other Anionic Surfactants

The solution may further comprise, consist essentially of, or consist of one or more other anionic surfactant chosen from sulfonated C12 to C22 carboxylic acids and alkali metal, ammonium, calcium and magnesium salts thereof, C6 to C22 alkyl diphenyl oxide sulfonic acids and alkali metal, ammonium, calcium and magnesium salts thereof, naphthalene sulfonic acids and alkali metal, ammonium, calcium and magnesium salts thereof, C8 to C22 alkyl sulfonic acids and alkali metal, ammonium, calcium and magnesium salts thereof, alkali metal, ammonium, calcium and magnesium C8 to C18 alkyl sulfates, and alkyl or alkenyl esters or diesters of sulfosuccinic acid in which the alkyl or alkenyl groups independently contain from six to eighteen carbon atoms and alkali metal, ammonium, calcium and magnesium salts thereof. Of the sulfonated C12 to C22 carboxylic acids and their aforesaid salts, sulfonated 9-octadecanoic acid, disodium 2-sulfo $C_{12}$-$C_{18}$ fatty acid salts and sodium methyl-2-sulfo $C_{12}$-$C_{16}$ esters are exemplary. An exemplary salt of naphthalene sulfonic acid is sodium alkyl naphthalene sulfonate. Exemplary salts of C8 to C22 alkyl sulfonic acids are sodium octyl (C8) sulfonate, sodium C14-C17 sec-alkyl sulfonate, and the sodium salts of 1-octane sulfonic acid, 1-decane sulfonic acid, and tridecane sulfonic acid. Of the aforesaid C8 to C18 alkyl sulfates, sodium lauryl sulfate and sodium octyl sulfate are exemplary.

Of the alkyl or alkenyl esters or diesters of sulfosuccinic acid in which the alkyl or alkenyl groups independently contain from six to eighteen carbon atoms and alkali metal, ammonium, calcium and magnesium salts thereof, disodium laureth sulfosuccinate and sodium dioctyl sulfosuccinate are exemplary.

Of the alkyl diphenyl oxide sulfonic acids, C6 and C10 alkylated sulfonated diphenyl oxide disodium salts are exemplary. Also exemplary are other alkylated sulfonated diphenyl oxide disodium salts, including dodecyl diphenyl oxide disulfonic acid and disodium 4-dodecylated diphenyl oxide sulfonate.

These ingredients are typically present in a concentration from about 0.1% w/w to about 20% w/w. Alternatively, minimum concentrations of from about 0.5% w/w, about 1% w/w, and about 2% w/w are contemplated. Maximum concentrations of about 15% w/w, about 13% w/w, about 11% w/w, about 10% w/w, about 9% w/w, about 7% w/w, about 5% w/w, about 3% w/w, and about 2.5% w/w are similarly contemplated.

Hydrogen Peroxide Stabilizers and Chelating Agents

At least one hydrogen peroxide stabilizer or chelating agent may be included to ensure that adequate levels of hydrogen peroxide in solution are maintained over time thereby prolonging shelf-life. Suitable hydrogen peroxide stabilizers include phosphoric acid ($H_3PO_4$) and phosphonic acids such as 1-hydroxyethylidene-1,1-diphosphonic acid (HEDP), amino tri(methylene phosphonic acid) (ATMP), diethylenetriamine penta(methylene phosphonic acid), 2-hydroxy ethylimino bis(methylene phosphonic acid), and ethylene diamine tetra(methylene phosphonic acid) (EDTMPA). Exemplary phosphonic acids are available from Rhodia (Cranbury, N.J.) under the trade mark BRIQUEST, while further exemplary phosphonic acids are available from ThermPhos (South Wales, UK) under the trade mark DEQUEST.

These ingredients are typically present in a concentration from about 0.1% w/w to about 20% w/w. Alternatively, minimum concentrations of from about 0.5% w/w, 1% w/w and about 2% w/w are contemplated. Maximum concentrations of about 15% w/w, about 13% w/w, about 11% w/w, about 10% w/w, about 9% w/w, about 7% w/w, about 5% w/w, about 3% w/w, and about 2.5% w/w are similarly contemplated.

Other Non-Ionic Surfactants

The solution can further comprise, consist essentially of, or consist of nonionic surfactants selected from alkyl polyglucosides, alkanolamines, ethoxylated alkanolamides, fatty acid esters, glycerol esters, and PEG esters, sorbitan esters, ethoxylated sorbitan esters, and alcohol ethoxylates.

These ingredients are typically present in a concentration from about 0.1% w/w to about 10% w/w. Alternatively, minimum concentrations of from about 0.5% w/w, about 1% w/w, and about 2% w/w are contemplated. Maximum concentrations of about 8% w/w, about 7% w/w, about 5% w/w, about 3% w/w, and about 2.5% w/w are similarly contemplated.

Buffering Agents

To achieve the desired preferred pH values (discussed further below), buffering agents may be added to the solution, at concentrations ranging from about 0.01% w/w to about 10% w/w. These buffering agents include phosphoric acid, acetic acid, lactic acid, and glycolic acid.

In the concentrated solution, the pH can be up to about 2. Alternatively, the pH can be up to about 1.5, or up to about 1.0. The pH can also be from about 0.05 or from about 0.2.

When diluted with water in situ, the solution can have a pH of from about 1.5 to about 5. Alternatively, the solution can have a pH of from about 1.7. Diluted solutions having a pH of up to about 4, up to about 3, or up to about 2.5, are also contemplated.

Corrosion Inhibitor

A corrosion inhibitor may be added for the purpose of improving compatibility of the solution with non-ferrous metals. Examples include triazoles, such as benzotriazole, hydrobenzotriazole, and carboxybenzotriazole. Further examples include sodium molybdate, sodium gluconate and sodium benzoate and combinations thereof. When included, the concentration, in concentrated solutions according to the invention, is from about 0.1% w/w to about 10% w/w. Concentrations from about 0.2% w/w are also contemplated. Concentrations of up to about 1.5% w/w, about 2.5% w/w, about 3.5% w/w, about 4.5% w/w, about 5% w/w, about 6% w/w and about 8% w/w are also contemplated.

Other Carboxylic Acids

One or more monocarboxylic acids and polycarboxylic acids known for their pH buffering, stabilizing or cleaning properties may also be added to the solution. Exemplary monocarboxylic acids are lactic acid, glycolic acid, acetic acid, 2-furoic acid, and 3-furoic acid. An exemplary polycarboxylic acid is citric acid.

When these other carboxylic acids are included in the concentrated solution, they are present in a concentration of from about 0.05% w/w to about 5% w/w of the solution. Alternatively, minimum concentrations of from about 0.5% w/w, about 1% w/w, and about 2% w/w are contemplated. Maximum concentrations of about 4.5% w/w, about 4% w/w, and about 3% w/w are also contemplated.

Other Additives

To enhance the marketable qualities of the product, additives such as coloring agents or dyes and scents or fragrances may be added.

INDUSTRIAL APPLICABILITY

Because hydrogen peroxide has a broad spectrum of activity, the present solution is useful in many different applications. In the healthcare field, the solution may be used in hospitals, clinics, laboratories, dental offices, home care and chronic care facilities. It may also be used in food and beverage processing and preparation, animal husbandry, the hospitality industry and for general sanitation, e.g. janitorial services.

The concentrated solutions described herein may be diluted with water at a ratio of from about 1:10 to about 1:1000 (solution/water). Typically, the solutions will be diluted in a ratio of about 1:64 or 1:32.

The present concentrated solutions can be provided in the form of a kit. For example, the various ingredients described above may be provided in the form of two or more separate parts that are mixed together prior to dilution and use.

The invention may be better understood with reference to the following non-limiting examples, in which the following ingredients are employed.

| | |
|---|---|
| Hydrogen peroxide and Water | |
| The hydrogen peroxide used in all the examples is a 50% w/w food grade commercial solution manufactured or sold by Arkema Inc. (Philadelphia, PA) | |
| DI water: | deionized water was used to make the aqueous solutions |
| Chelating Agents | |
| Dequest 2010: | 1-hydroxyethylidene-1,1-diphosphonic acid (60% w/w solution) manufactured or sold by ThermPhos (South Wales, UK) |
| Salicylic acid | |
| Anionic Surfactants | |
| Biosoft S-101: | dodecyl benzene sulfonic acid (DDBSA) (98% w/w solution) manufactured or sold by Stepan Company (Northfield, IL) |
| Bioterge PAS-8S: | sodium octyl sulfonate (SOS) (40% w/w solution) manufactured or sold by Stepan Company (Northfield, IL) |
| Aerosol OT-75: | sodium dioctyl sulfosuccinate (75% w/w solution) manufactured or sold by Cytec Industries Inc. (West Paterson, NJ) |
| Stepanol AM: | ammonium lauryl sulfate (30% w/w solution) manufactured or sold by Stepan Company (Northfield, IL) |
| Sparingly Soluble Carboxylic Acids | |
| salicylic acid | |
| benzoic acid | |
| Non-ionic Surfactants (Emulsifiers) | |
| Alfonic L610-3.5: | C6-C10 alkyl, 3.5 moles of ethylene oxide (EO) alcohol ethoxylate (AE) (100% w/w solution) manufactured or sold by Sasol North America Inc. (Houston, TX) |
| Surfynol 104 PG-50: | tetramethyl-5-decyne-4,7-diol, 2,4,7,9, as a 50% w/w solution in propylene glycol. manufactured or sold by Air Products (Allentown, PA) |

-continued

| Surfynol 420: | tetramethyl-5-decyne-4,7-diol, 2,4,7,9 (25% w/w solution), ethoxylated tetramethyl-5-decyne-4,7-diol, 2,4,7,9 (75% w/w solution) manufactured or sold by Air Products (Allentown, PA) |
| --- | --- |
| Surfynol 440: | ethoxylated tetramethyl-5-decyne-4,7-diol, 2,4,7,9 (100% w/w solution) manufactured or sold by Air Products (Allentown, PA) |
| Ninol 40-CO: | cocamide diethanolamide (85% w/w solution) manufactured or sold by Stepan Company (Northfield, IL) |
| Ninol 30-LL: | lauramide diethanolamide (85% w/w solution) manufactured or sold by Stepan Company (Northfield, IL) |
| Ninol 11-CM: | coconut diethanolamide (60% w/w solution) manufactured or sold by Stepan Company (Northfield, IL) |
| APG 325: | D-glucopyranoside, C9-C11 alkyl, oligomeric (50% w/w solution) manufactured or sold by Cognis GmbH (Monheim, Germany) |
| Glucopon 425N: | a mixture of alkyl polyglucoside, D-glucopyranoside, C10-C16 alkyl, oligomeric, 20% w/w D-glucose, decyl, octyl ethers, oligomeric (30% w/w solution) manufactured or sold by Cognis GmbH (Monheim, Germany) |
| Glucopon 600UP: | alkyl polyglucoside, D-glucopyranoside, C10-C16 alkyl, oligomeric (50% w/w solution) manufactured or sold by Cognis GmbH (Monheim, Germany) |
| Levenol H&B: | glyceryth-2-cocoate (100% w/w solution) manufactured or sold by Kao Corporation (Cincinnati, OH) |
| Emanon XLF: | glycereth-7-caprilate/caprate (100% w/w solution) manufactured or sold by Kao Corporation (Cincinnati, OH) |
| Oxidet DM-20: | dimethyl lauramine oxide (30% w/w solution) manufactured or sold by Kao Corporation (Cincinnati, OH) |
| Ethox TAM-15 | PEG-15 tallow ammonium ethosulfate manufactured or sold by Ethox Chemicals (Greenville, SC) |
| Ethox TAM-20 | POE (20) tallow amine manufactured or sold by Ethox Chemicals (Greenville, SC) |
| Ethal OA 23 | Oleyl (C18) alcohol ethoxylate, 23 moles of EO/mole of alcohol (70% w/w solution) manufactured or sold by Ethox Company (Greenville, SC) |
| Tomadol 91-2.5 | C9-C11 alcohol ethoxylated (90% w/w solution) manufactured or sold by Tomah Products Inc., Reserve, LA |
| Tomadol 91.6 | C9-C11 alcohol ethoxylated (90% w/w solution) manufactured or sold by Tomah Products Inc., Reserve, LA |
| Tomadol 91.8 | C9-C11 alcohol ethoxylated (100% w/w solution) manufactured or sold by Tomah Products Inc., Reserve, LA |
| Rhodasurf ON-877 | Polyethylene glycol monooleyl ether (70% w/w solution) manufactured or sold by Rhodia Cranbury NJ |

Pluronics used in the following examples are all block copolymers of EO-PO manufactured or sold by BASF Corporation. These compounds are more fully described above.

Tetronics used in the following examples are all block copolymers manufactured or sold by BASF Corporation. These compounds are more fully described above.

| Anionic Surfactants (Hydrotropes) | |
| --- | --- |
| Stepanate SXS: | sodium xylene sulfonate (40% w/w solution) manufactured or sold by Stepan Company (Northfield, IL) |
| Dowfax C10L: | C10 alkylated sulfonated diphenyl oxide disodium salt (40% w/w solution) manufactured or sold by Dow Chemical Company |
| DOWFAX C6L | C6 alkylated sulfonated diphenyl oxide disodium salt (40% w/w solution) (also called Dowfax hydrotrope) manufactured or sold by Dow Chemical Company |

| Solvents | |
| --- | --- |
| Dowanol PnP: | propylene glycol, n-propyl ether (100% w/w solution) manufactured or sold by Dow Chemical Company |
| Dowanol TPnB | tripropylene glycol, n-butyl ether (100% w/w solution) manufactured or sold by Dow Chemical Company |
| Dowanol DPnP: | dipropylene glycol, n-propyl ether (100% w/w solution) manufactured or sold by Dow Chemical Company |
| 1,3 butylene glycol | |
| Isopropyl alcohol | |
| Benzyl alcohol | |
| Methoxy methyl butanol (MMB) | |

| pH Adjusters/Buffers |
| --- |
| Phosphoric acid |

Microbial Test Methods And Organisms

Tests were conducted using the following test organisms: *Pseudomonas aeruginosa* (ATCC 15442), *Staphylococcus aureus* (ATCC 6538), *Salmonella choleraesuis* (ATCC 10708), *Mycobacterium terrae* (ATCC 15755), *Trichophyton mentagrophytes* (ATCC 9533), and the Sabin vaccine strain of polio virus type 1 (ATCC VR-192).

Solutions were tested using ASTM E2111 (Standard Quantitative Carrier Test Method To Evaluate the Bactericidal, Fungicidal, Mycobactericidal and Sporicidal Potencies of Liquid Chemical Germicides, ASTM International, 2005), and ASTM E1053/97 (Standard Test Method for Efficacy of Virucidal Agents Intended for Inanimate Environmental Surfaces, ASTM International, 2002).

Physical Stability Test Method

Freeze/thaw tests were performed to evaluate the physical stability of the solution. Samples were placed in a freezer at −15° C. for at least 12 hours and then thawed at room temperature for about 8 hours. The crystallization or precipitation of each sample was visually observed and recorded.

Chemical Stability Test Method

Solutions were tested for their peroxide content immediately after sample preparation. The tests were repeated at different time intervals at room temperature. The results were then extrapolated to calculate the peroxide loss and pH change of the solutions over a one year period.

For ease of review, all concentrations listed in the below tables are actual concentrations of the ingredients in the solutions, and not the amount of starting raw material used to make the solutions.

Example I

Exemplary solutions were prepared as shown in Tables 3, 4, 5, 6 and 7 below.

TABLE 3

| Ingredient | Solution | | | | | | | |
| --- | --- | --- | --- | --- | --- | --- | --- | --- |
| | A1 % w/w | A2 % w/w | A3 % w/w | A4 % w/w | A5 % w/w | A6 % w/w | A7 % w/w | A8 % w/w |
| DI water | Qs to 100 | | | | | | | |
| Biosoft S-101 | 10.00 | | | | | | | |

TABLE 3-continued

| Ingredient | A1 % w/w | A2 % w/w | A3 % w/w | A4 % w/w | A5 % w/w | A6 % w/w | A7 % w/w | A8 % w/w |
|---|---|---|---|---|---|---|---|---|
| Dowanol PnP | | | | | 8.00 | | | |
| Hydrogen peroxide | | | | | 7.5 | | | |
| Salicylic acid | | | | | 2.50 | | | |
| Pluronic 17R2 | 5 | 0 | 0 | 0 | 0 | 0 | 0 | 0 |
| Pluronic 17R4 | 0 | 5 | 0 | 0 | 0 | 0 | 0 | 0 |
| Pluronic 25R2 | 0 | 0 | 5 | 0 | 0 | 0 | 0 | 0 |
| Pluronic 31R1 | 0 | 0 | 0 | 5 | 0 | 0 | 0 | 0 |
| Pluronic L43 | 0 | 0 | 0 | 0 | 5 | 0 | 0 | 0 |
| Pluronic L44 | 0 | 0 | 0 | 0 | 0 | 5 | 0 | 0 |
| Pluronic L61 | 0 | 0 | 0 | 0 | 0 | 0 | 5 | 0 |
| Pluronic L62 | 0 | 0 | 0 | 0 | 0 | 0 | 0 | 5 |

TABLE 4

| Ingredient | A9 % w/w | A10 % w/w | A11 % w/w | A12 % w/w |
|---|---|---|---|---|
| DI water | Qs to 100 | Qs to 100 | Qs to 100 | Qs to 100 |
| Biosoft S-101 | 10.00 | 10.00 | 10.00 | 10.00 |
| Dowanol PnP | 8.00 | 8.00 | 8.00 | 8.00 |
| Hydrogen peroxide | 7.5 | 7.5 | 7.5 | 7.5 |
| Salicylic acid | 2.50 | 2.50 | 2.50 | 2.50 |
| Pluronic L64 | 5 | 0 | 0 | 0 |
| Pluronic F68 | 0 | 5 | 0 | 0 |
| Pluronic L81 | 0 | 0 | 5 | 0 |
| Pluronic L101 | 0 | 0 | 0 | 5 |

TABLE 5

| Ingredient | A13 % w/w | A14 % w/w | A15 % w/w | A16 % w/w | A17 % w/w | A18 % w/w | A19 % w/w | A20 % w/w | A21 % w/w | A22 % w/w |
|---|---|---|---|---|---|---|---|---|---|---|
| DI water | | | | | Qs to 100 | | | | | |
| Biosoft S-101 | 5 | 8 | 10 | 10 | 14 | 10 | 12 | 12 | 9 | 10 |
| Phosphoric acid | 0 | 3.75 | 0 | 6.75 | 0 | 0 | 0 | 0 | 0 | 0 |
| Dequest 2010 | 0 | 0.5 | 0 | 0 | 0 | 0 | 0 | 0 | 0 | 0 |
| Dowanol PnP | 8 | 7 | 4 | 8 | 8 | 5 | 4 | 15 | 7.5 | 8 |
| 1,3 butylene glycol | 0 | 0 | 0 | 0 | 0 | 4 | 5 | 0 | 0 | 0 |
| Hydrogen peroxide | 4 | 5 | 7.5 | 7.5 | 7.5 | 7.5 | 5 | 6 | 7 | 7 |
| Salicylic acid | 1 | 2.8 | 2.5 | 2.5 | 2.5 | 2.5 | 1.75 | 2.5 | 0 | 2.5 |
| Benzoic acid | 0 | 0 | 0 | 0 | 0 | 0 | 0 | 2.5 | 2.4 | 1.5 |
| Pluronic L62 | 3.5 | 7 | 5 | 5 | 5 | 5 | 6 | 5.3 | 4.8 | 5 |

TABLE 6

| Ingredient | A23 % w/w | A24 % w/w | A25 % w/w | A26 % w/w | A27 % w/w | A28 % w/w | A29 % w/w |
|---|---|---|---|---|---|---|---|
| DI water | | | | Qs to 100 | | | |
| Biosoft S-101 | 7 | 8 | 10 | 10 | 14 | 10 | 12 |
| Phosphoric acid | 6.75 | 3.5 | 0 | 6.75 | 0 | 0 | 0 |
| Dequest 2010 | 0 | 0.5 | 0 | 0 | 0 | 0 | 0 |
| Dowanol PnP | 8 | 7 | 9 | 10 | 8 | 7 | 9 |
| Hydrogen peroxide | 4 | 5 | 7.5 | 7.5 | 7.5 | 7.5 | 5 |
| Salicylic acid | 2 | 2.8 | 2.5 | 2.5 | 2.5 | 2.5 | 1.75 |
| Tetronic 901 | 5 | 0 | 0 | 0 | 0 | 0 | 0 |
| Tetronic 904 | 0 | 5 | 0 | 0 | 0 | 0 | 0 |
| Tetronic 908 | 0 | 0 | 5 | 0 | 0 | 0 | 0 |
| Tetronic 701 | 0 | 0 | 0 | 5 | 0 | 0 | 0 |
| Tetronic 150R1 | 0 | 0 | 0 | 0 | 5 | 0 | 0 |
| Tetronic 1301 | 0 | 0 | 0 | 0 | 0 | 5 | 0 |
| Tetronic 1307 | 0 | 0 | 0 | 0 | 0 | 0 | 5 |

TABLE 7

| Ingredient | A30 % w/w | A31 % w/w | A32 % w/w | A33 % w/w | A34 % w/w | A35 % w/w | A36 % w/w |
|---|---|---|---|---|---|---|---|
| DI water | | | | Qs to 100 | | | |
| Biosoft S-101 | 7 | 8 | 10 | 10 | 10 | 10 | 10 |
| Dequest 2010 | 0 | 0.5 | 0 | 0 | 0 | 0 | 0 |
| Dowanol PnP | 8 | 7 | 10 | 0 | 0 | 0 | 0 |
| Isopropyl alcohol | 0 | 0 | 0 | 11 | 0 | 0 | 0 |
| Dowanol TPnB | 0 | 0 | 0 | 0 | 8 | 0 | 0 |
| Dowanol DPnP | 0 | 0 | 0 | 0 | 0 | 8 | 0 |
| Benzyl alcohol | 0 | 0 | 0 | 0 | 0 | 0 | 8 |
| Hydrogen peroxide | 4 | 5 | 7.5 | 4 | 5 | 7.5 | 0.5 |
| Salicylic acid | 2.5 | 2.8 | 2.5 | 3.0 | 0 | 2 | 2.7 |
| Benzoic acid | 1.5 | 0 | 2 | 0 | 2.5 | 0 | 0 |
| Pluronic L62 | 5 | 5 | 5 | 4 | 6 | 4.5 | 5 |

The above solutions have a pH of from about 0.05 to about 1.5.

Solutions A1-A19 were tested for their physical stability and remained clear after the freeze/thaw test. No precipitation was observed. The freeze/thaw test was repeated five times and all sample solutions remained clear.

Solutions A8, A16, and A17 were tested for bactericidal, virucidal, fungicidal, and mycobactericidal activity. Bactericidal, virucidal, and fungicidal tests were performed at 1:64 dilution, and mycobactericidal tests were conducted at 1:32 dilution. All tests were conducted at a contact time of 5 minutes and at a temperature of 20° C.±2. All test organisms were first suspended in bovine serum at a final concentration of 5% w/w of the solution. Water with a standard hardness of 400 ppm as calcium carbonate was used as the diluent. The water was prepared according to the formula in AOAC International (1990). The results are illustrated in Table 8 below:

TABLE 8

| Microorganism | Test method | Log reduction | | |
|---|---|---|---|---|
| | | Solution A8 | Solution A16 | Solution A17 |
| Staphylococcus aureus (ATCC 6538) | ASTM E2111-00 | >6 | >6 | >6 |
| Salmonella choleraesuis (ATCC 10708) | ASTM E2111-00 | >6 | >6 | >6 |
| Pseudomonas aeruginosa (ATCC 15442) | ASTM E2111-00 | >6 | >6 | >6 |
| Trichophyton mentagrophytes (ATCC 9533) | ASTM E2111-00 | >5 | >5 | >5 |
| Poliovirus type 1 (ATCC VR-192) | ASTM E1053 | >3 | >3 | >3 |
| Mycobacterium terrae (ATCC-15755) | ASTM E2111-00 | >5 | >5 | >5 |

The above results demonstrate that exemplary solutions A8, A16, and A17 were effective in achieving a greater than 6 log reduction in bacterial counts, a greater than 3 log reduction in viral counts, and a greater than 5 log reduction in mycobacterial counts after a 5 minute contact time.

Solutions A8, A16, A17 were tested for hydrogen peroxide stability at room temperature. After one year, these solutions had less than 4% peroxide loss.

Example II

The following comparative examples show that replacing ingredients in the present solutions with other ingredients belonging to the same chemical class may result in precipitation of the cyclic carboxylic acid, either following the first or second freeze/thaw test, or immediately after preparation of the solution. As demonstrated above, the combination of alkyl benzene sulfonic acid, block copolymers and a solvent provides a stable concentrated solution. Interestingly, although alkyl benzene sulfonic acid is an anionic surfactant, the substitution of alkyl benzene sulfonic acid with other anionic surfactants resulted in phase separation (precipitation). In addition, although a block-copolymer is a non-ionic surfactant, the substitution of the block copolymer with other non-ionic surfactants resulted in phase separation (precipitation). Furthermore, when solvents were removed from the solution and replaced with higher concentrations of emulsifiers, the resulting solution precipitated.

Comparative solutions B1 to B46, detailed in Tables 9 through 14, were prepared and tested for their physical stability. The solutions either turned turbid after preparation, or precipitated after the second freeze/thaw test. Only solution B41 remained clear and did not precipitate even after freeze/thaw, but the composition is not in accordance with the invention, as explained below.

TABLE 9

| Ingredient | Solution | | |
|---|---|---|---|
| | B1 % w/w | B2 % w/w | B3 % w/w |
| DI water | QS to 100 | | |
| Biosoft S-101 | 10 | | |
| Dowanol PnP | 8 | | |
| Hydrogen peroxide | 7.5 | | |

TABLE 9-continued

| Ingredient | Solution | | |
|---|---|---|---|
| | B1 % w/w | B2 % w/w | B3 % w/w |
| Salicylic acid | 2.5 | | |
| Dowfax C10L | 2 | 0 | 0 |
| Dowfax C6L | 0 | 2 | 0 |

TABLE 10

| Ingredient | Solution | | | | | |
|---|---|---|---|---|---|---|
| | B4 % w/w | B5 % w/w | B6 % w/w | B7 % w/w | B8 % w/w | B9 % w/w |
| DI water | Qs to 100 | | | | | |
| Biosoft S-101 | 10.00 | | | | | |
| Dowanol PnP | 8.00 | | | | | |
| Hydrogen peroxide | 7.5 | | | | | |
| Salicylic acid | 2.50 | | | | | |
| Ethox TAM-15 | 5 | 0 | 0 | 0 | 0 | 0 |
| Ethox TAM-20 | 0 | 5 | 0 | 0 | 0 | 0 |
| Dowfax C10L | 0 | 0 | 2 | 0 | 0 | 0 |
| Dowfax C6L | 0 | 0 | 0 | 2 | 0 | 0 |
| Ninol 40-CO | 0 | 0 | 0 | 0 | 4.3 | 0 |
| Ninol 30-LL | 0 | 0 | 0 | 0 | 0 | 4 |

TABLE 11

| Ingredient | Solution | | | | | | | |
|---|---|---|---|---|---|---|---|---|
| | B10 % w/w | B11 % w/w | B12 % w/w | B13 % w/w | B14 % w/w | B15 % w/w | B16 % w/w | B17 % w/w |
| DI water | Qs to 100 | | | | | | | |
| Biosoft S-101 | 10.00 | | | | | | | |
| Dowanol PnP | 8.00 | | | | | | | |
| Hydrogen peroxide | 7.5 | | | | | | | |
| Salicylic acid | 2.50 | | | | | | | |
| Rhodasurf ON-877 | 3.5 | 0 | 0 | 0 | 0 | 0 | 0 | 0 |
| Tomadol 91-2.5 | 0 | 5 | 0 | 0 | 0 | 0 | 0 | 0 |
| Oxidet DM-20 | 0 | 0 | 1.5 | 0 | 0 | 0 | 0 | 0 |
| Alfonic L610-3.5 | 0 | 0 | 0 | 5 | 0 | 0 | 0 | 0 |
| Ethal OA 23 | 0 | 0 | 0 | 0 | 3.5 | 0 | 0 | 0 |
| Surfynol 104 PG-50 | 0 | 0 | 0 | 0 | 0 | 2.5 | 0 | 0 |
| Surfynol 420 | 0 | 0 | 0 | 0 | 0 | 0 | 5 | 0 |
| Surfynol 440 | 0 | 0 | 0 | 0 | 0 | 0 | 0 | 5 |

TABLE 12

| Ingredient | Solution B18 % w/w | B19 % w/w | B20 % w/w | B21 % w/w | B22 % w/w | B23 % w/w | B24 % w/w | B25 % w/w | B26 % w/w |
|---|---|---|---|---|---|---|---|---|---|
| DI water | | | | | Qs to 100 | | | | |
| Biosoft S-101 | | | | | 10.00 | | | | |
| Dowanol PnP | | | | | 8.00 | | | | |
| Hydrogen peroxide | | | | | 7.5 | | | | |
| Salicylic acid | | | | | 2.50 | | | | |
| Levenol H&B | 5 | 0 | 0 | 0 | 0 | 0 | 0 | 0 | 0 |
| Aerosol OT-75 | 0 | 3.5 | 0 | 0 | 0 | 0 | 0 | 0 | 0 |
| Bioterge PAS-8S | 0 | 0 | 2 | 0 | 0 | 0 | 0 | 0 | 0 |
| Stepanate SXS | 0 | 0 | 0 | 3.5 | 0 | 0 | 0 | 0 | 0 |
| Stepanol AM | 0 | 0 | 0 | 0 | 1.5 | 0 | 0 | 0 | 0 |
| Ninol 11-CM | 0 | 0 | 0 | 0 | 0 | 3.0 | 0 | 0 | 0 |
| Tomadol 91.8 | 0 | 0 | 0 | 0 | 0 | 0 | 5 | 0 | 0 |
| Tomadol 91.6 | 0 | 0 | 0 | 0 | 0 | 0 | 0 | 5 | 0 |
| Emanon XLF | 0 | 0 | 0 | 0 | 0 | 0 | 0 | 0 | 5 |

The pH of Solutions B1 to B26 was from 0.5 to 1.5. In these solutions, block copolymer surfactants were replaced with different non-ionic and anionic surfactants. Additionally, a solvent was added to each solution. All solutions became turbid immediately after preparation or precipitated after the freeze/thaw test.

TABLE 13

| Ingredient | Solution B27 % w/w | B28 % w/w | B29 % w/w | B30 % w/w | B31 % w/w | B32 % w/w | B33 % w/w | B34 % w/w | B35 % w/w |
|---|---|---|---|---|---|---|---|---|---|
| DI water | | | | | Qs to 100 | | | | |
| Hydrogen peroxide | | | | | 7.5 | | | | |
| Dowanol PnP | 8.0 | | | | | | 0 | | |
| Salicylic acid | 2.5 | | | | | 2.0 | 2.5 | 2.5 | 2.5 |
| Pluronic L62 | 5.0 | | | | | 5.0 | 7 | 8 | 10 |
| Dequest 2010 | 6 | 6 | 6 | 6 | 6 | 0 | 0 | 0 | 0 |
| Dowfax C6L | 4 | 0 | 0 | 0 | 0 | 0 | 0 | 0 | 0 |
| Dowfax C10L | 0 | 4 | 0 | 0 | 0 | 0 | 0 | 0 | 0 |
| Stepanol AM | 0 | 0 | 3 | 0 | 0 | 0 | 0 | 0 | 0 |
| Bioterge PAS-8S | 0 | 0 | 0 | 4 | 0 | 0 | 0 | 0 | 0 |
| Stepanate SXS | 0 | 0 | 0 | 0 | 4 | 0 | 0 | 0 | 0 |
| Biosoft S101 | 0 | 0 | 0 | 0 | 0 | 10 | 12 | 14 | 10 |

Solutions B27 to B31 did not have Biosoft S101 (dodecyl benzene sulfonic acid), and instead incorporated other anionic surfactants. Solutions B32 to B35 did not have solvent. Solutions B27 to B35 turned turbid immediately after preparation or precipitated after the second freeze/thaw.

TABLE 14

| Ingredient | Solution B36 % w/w | B37 % w/w | B38 % w/w | B39 % w/w | B40 % w/w | B41 % w/w | B42 % w/w | B43 % w/w | B44 % w/w | B45 % w/w | B46 % w/w |
|---|---|---|---|---|---|---|---|---|---|---|---|
| DI water | | | | | | Qs to 100 | | | | | |
| Salicylic acid | | | | | | 2.5 | | | | | 2 |
| Hydrogen peroxide | | | | | | 7 | | | | | 3 |
| Dequest 2010 | | | 6 | | | | 0 | 0 | 0 | 0 | 0 |
| Dowanol PnP | 20 | 35 | 50 | 0 | 0 | 0 | 15 | 0 | 0 | 7 | 0 |
| Isopropyl alcohol | 0 | 0 | 0 | 20 | 35 | 50 | 0 | 11 | 0 | 0 | 0 |
| Methoxy methyl butanol (MMB) | 0 | 0 | 0 | 0 | 0 | 0 | 0 | 0 | 15 | 0 | 0 |
| Biosoft S101 | 0 | 0 | 0 | 0 | 0 | 0 | 10 | 10 | 10 | 10 | 14 |
| Ethal OA 23 | 0 | 0 | 0 | 0 | 0 | 0 | 0 | 0 | 0 | 6 | 0 |
| Pluronic L62 | 0 | 0 | 0 | 0 | 0 | 0 | 0 | 0 | 0 | 0 | 5 |

Solutions B36 to B38 did not form a one phase solution, and resulted in two phases immediately after preparation. Solutions B39, B40 precipitated immediately after mixing. Only solution B41 remained clear even after freeze/thaw. This solution contained 50% w/w isopropyl alcohol, and is therefore a flammable solution.

The above experiments show that unless the right mixture of ingredients is employed, it is necessary to use very high levels of solvents to achieve a one-phase solution. As mentioned above, solutions containing a high solvent content can be hazardous.

The foregoing examples are by way of illustration only and shall not be construed to limit the scope of the invention as defined by the following claims.

The invention claimed is:

1. A concentrated and stable cleaning and disinfecting solution having a pH of from about 0.05 to about 2, comprising:
   a. from about 2% w/w to about 8% w/w hydrogen peroxide;
   b. from about 5% w/w to about 20% w/w of at least one C8-C16 linear alkyl aryl sulfonic acid;
   c. from about 0.5% w/w to about 5% w/w of at least one sparingly soluble cyclic carboxylic acid, wherein the cyclic carboxylic acid is present in acid and salt form in a ratio of at least 9:1 (acid:salt);
   d. from about 2% w/w to about 10% w/w of at least one block copolymer surfactant; and
   e. from about 4% w/w to about 15% w/w of at least one solvent;
      wherein the solution is stable.

2. The solution of claim 1, wherein the hydrogen peroxide concentration is from about 3% w/w to about 8% w/w.

3. The solution of claim 1, wherein the pH is from about 0.2 to about 2.

4. The solution of claim 1, wherein the sparingly soluble carboxylic acid is chosen from benzoic acid and benzoic acid derivatives.

5. The solution of claim 4, wherein the benzoic acid derivative is salicylic acid.

6. The solution of claim 1, wherein the solvent is chosen from glycol ethers, short chain alcohols having from 1 to 8 carbon atoms, benzyl alcohol, and phenoxy ethanol.

7. The solution of claim 6, wherein the glycol ethers are chosen from propylene glycol n-propyl ether, dipropylene glycol n-propyl ether, propylene glycol methyl ether, dipropylene glycol methyl ether, tripropylene glycol monomethyl ether, dipropylene glycol n-propyl ether, tripropylene glycol n-propyl ether, dipropylene glycol n-butyl ether, tripropylene glycol n-butyl ether, ethylene glycol monobutyl ether, ethylene glycol monohexyl ether, and diethylene glycol monobutyl ether.

8. The solution of claim 7, comprising propylene glycol n-propyl ether.

9. The solution of claim 1, wherein the C8-C16 linear alkyl aryl sulfonic acid is dodecylbenzene sulfonic acid.

10. The solution of claim 1, wherein the at least one block copolymer surfactant is chosen from (A)-(B)-(A) or (B)-(A)-(B) or

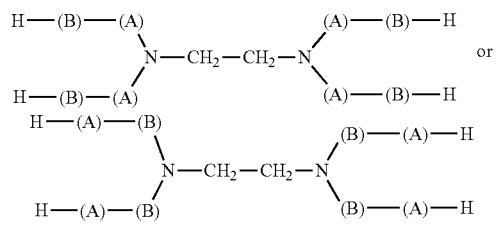

i. wherein A represents a block of propylene oxide repeating units and B represents a block of ethylene oxide repeating units, and wherein the block copolymer surfactant has a molecular weight of from 1500 to 30000 Daltons.

11. The solution of claim 10, wherein the at least one block copolymer surfactant is a block copolymer with an average molecular weight of about 2500 Daltons, total weight of propylene oxide units of about 2000 Daltons and EO % of about 20%.

12. The solution according to claim 1, diluted with water at a ratio of from 1:10 to 1:1000 (solution:water).

* * * * *